United States Patent [19]
Pavia et al.

[11] Patent Number: 5,847,206
[45] Date of Patent: *Dec. 8, 1998

[54] AMPHIPHILIC FLUORINE DERIVATIVES WITH TELOMERIC STRUCTURES; PREPARATION PROCEDURE AND BIOMEDICAL APPLICATIONS

[75] Inventors: Andre Pavia, Villeneuve-lez-Avignon; Bernard Pucci, Molleges; Jean G. Riess, Falicon; Leila Zarif, Nice, all of France

[73] Assignee: Alliance Pharmaceutical Corp., San Diego, Calif.

[*] Notice: The term of this patent shall not extend beyond the expiration date of Pat. No. 5,527,962.

[21] Appl. No.: 483,289

[22] Filed: Jun. 7, 1995

Related U.S. Application Data

[63] Continuation of Ser. No. 238,970, May 5, 1994, Pat. No. 5,527,962, which is a continuation of Ser. No. 741,749, Aug. 7, 1991, abandoned.

[30] Foreign Application Priority Data

Aug. 9, 1990 [FR] France ................... 90 10206

[51] Int. Cl.$^6$ ............... C07C 229/04; C07C 233/05
[52] U.S. Cl. ............... 562/575; 536/4.1; 562/562; 564/95; 564/96; 564/152; 564/153; 564/154; 564/158; 564/197; 564/201
[58] Field of Search .................. 564/152, 153, 564/154, 158, 95, 96, 197, 201; 562/575, 562; 536/4.1

[56] References Cited

U.S. PATENT DOCUMENTS

| | | | |
|---|---|---|---|
| 4,089,804 | 5/1978 | Falk ................ | 252/355 |
| 4,460,804 | 7/1984 | Kleiner et al. ........... | 252/8.05 |
| 4,985,550 | 1/1991 | Charpiot et al. ......... | 536/18.4 |
| 5,527,962 | 6/1996 | Pavia et al. ............. | 564/152 |

FOREIGN PATENT DOCUMENTS 9101521  4/1991  European Pat. Off. .

OTHER PUBLICATIONS

Klein, J. and Herzog, D., (1987) Synthesis of some poly-(vinylsaccharides)s of the amide type and investigation of their solution properties. Macromolec. Chem 188:1217–1232.

Le Blanc, M., et al., (1985) Use of lymphoblastoid namalva cell cultures in a toxicity test. Application to monitoring of detoxification procedures for fluorocarbons to be used as intravascular oxygen–carriers. Pharmaceutical Research 246–248.

Le Blanc, M., et al., (1988) Pharm. Res. pp. 195–209.

Long, D. Carl et al., Preparation and application of highly concentrated perfluoroctylbromide fluorocarbon emulsions. Blood Substitutes (T. Chang and R. Geyer, eds.) Marcel Dekker, Inc., New York, 1989. pp. 441–442.

Menger, F., and Portnoy, (1967) On the chemistry of reactions proceeding inside molecular aggregates. J. Am Chem. Soc. 89:4698–4703.

Riess, J. and Le Blanc, M., (1988) Chap. 5 in Blood Substitutes: Preparation, Physiology and Medical Applications, (K.C. Lowe, ed.), Ellis Horwood, Cichester.

Riess, J.G., (1987) Orientations Actuelles en Matière de Transporteur d'Oxygène in vivo, les Emulsions de Fluorocarbures, J. Chim. Phys. 84(9), 1119–1127.

Riess, J.G., et al., (1989) in Blood Substitutes, op. cit. pp. 421–430.

Riess, J.G., (1988) Blood substitutes: where do we stand with the fluorocarbon approach? Curr. Surg. 45:365–370.

*Primary Examiner*—Shailendra Kumar
*Attorney, Agent, or Firm*—Knobbe, Martens, Olson & Bear, LLP

[57] ABSTRACT

New fluorinated derivatives useful as surfactants or in the transport of drug or markers, or in drug targeting, and preparations containing the derivatives, for medical, cosmetic and veterinary uses, having the formula:

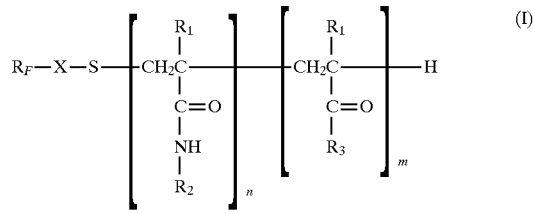

wherein $R_F$ is a fluorinated radical, X is a linear or branched alkylene, $R^1$ is H or $CH_3$, $R^2$ is a radical having at least one OH group, $R^3$ is a radical derived from an amino acid or a peptide, $1 \leq n \leq 50$ and $0 \leq m \leq 200$ with $0.2 \leq n/n+m \leq 1$.

These derivatives can be used as prodrugs or in formulating pharmaceutical, cosmetic and veterinary preparations, in biology and medicine, notably in compositions acting as carriers of oxygen and other gases, of contrast agents, or as carriers of substances used in therapy, or as carriers of markers.

12 Claims, 2 Drawing Sheets

AMPHIPHILIC FLUORINE DERIVATIVES WITH TELOMERIC STRUCTURES; PREPARATION PROCEDURE AND BIOMEDICAL APPLICATIONS

This application is a continuation of U.S. patent application Ser. No. 08/238,970, filed May 5, 1994, now U.S. Pat. No. 5,527,962, a continuation of U.S. patent application Ser. No. 07/741,749, filed Aug. 7, 1991, now abandoned.

The present invention relates to new amphiphilic fluorine derivatives having telomeric structures, methods for their preparation, and biomedical applications.

It relates particularly to the synthesis of biocompatible fluorinated amphiphilic derivatives useful in formulations for pharmaceutical, cosmetic, veterinary or phytosanitary use, or in biology and medicine, and other uses, for example, as prodrugs, or in preparations capable of acting as gas carriers for biomedical use, as contrast agents, or media for the transport and targeting of drugs.

BACKGROUND OF THE INVENTION

It is well known that cells of human tissues and organs die when they are deprived of the oxygen supplied by blood, as in hemorrhages, severe anemia, or cerebral or myocardial ischemia. Until now, the only efficient way of replacing the necessary oxygen was by blood transfusion; however, transfusion is inappropriate in some pathological or clinical cases; moreover, it almost always presents certain immunological and infectious risks. Research was therefore undertaken aiming at the preparation of satisfactory in vivo oxygen carriers which could not only replace the erythrocyte function to transport and deliver oxygen, but also be used in situations where the administration of red blood cells is ineffective or contra-indicated.

Substances capable of carrying oxygen in a dissolved form are known: they are the fluorocarbons, which are the best-known solvents of gases and also among the most inert compounds that can be prepared. This type of product is described by J. G. Riess and M. Le Blanc, in "Blood Substitutes: Preparation, Physiology and Medical Applications," Chap. 5 (K. C. Lowe, Ed., Ellis Horwood, Cichester, 1988), and by J. G. Riess in "Orientations Actuelles en Matiere de Transporteurs d'oxygene in vivo, les Emulsions de Fluorocarbures," J. Chim. Phys. 84(9), 1119–1127 (1987). Some fluorocarbon preparations can simultaneously fulfill yet other functions, e.g. as contrast agents in diagnosis or as drug carriers. However, the intravascular use of fluorocarbons requires that they be prepared in a dispersed form, for example, an emulsion, because fluorocarbons are not water-soluble. Such an emulsion usually comprises a fluorocarbon-based oxygen-carrier, one or more surfactants, water, and other ingredients, such as inorganic salts, to adjust the pH and the osmotic and oncotic pressures. Also the emulsion must comprise cryoprotectors if the emulsion is to be frozen. Other additives, such as nutritive agents, vitamins, steroids, prostaglandins, antibiotics, and thrombolytic agents may be required to meet specific therapeutic requirements.

In such emulsions, the fluorocarbons are dispersed in the form of droplets of about 0.2 μm, by means of one or more surfactants. Different emulsions have been developed such as Fluosol-DA® or Fluosol®, developed by the Green Cross Corporation in Japan, and the more concentrated fluorocarbon emulsions developed by Alliance Pharmaceutical, Inc. and described by C. Long, D. Long, J. G. Riess, R. Follana, A. Burgan and R. Mattrey in: "Blood Substitutes," edited by T. M. S. Chang and R. P. Geyer (Marcel Dekker, Inc., New York, 1989), pp. 441–442. Certain disadvantages and/or limitations in emulsions of this type are described by J. G. Riess, C. Arlen, J. Greiner, M. Le Blanc, A. Manfredi, S. Pace, C. Varescon and L. Zarif, in: "Blood Substitutes," edited by T. M. S. Chang and R. P. Geyer (Marcel Dekker Inc., New York, 1989), pp. 421–430; and by J. G. Riess in Curr. Surg. 45, 365 (1988).

It is a fact that the surfactants used are polydisperse, and badly defined. Moreover, one of them, Pluronic F-68®, the main surfactant in Fluosol-DA, causes a transitory anaphylactic reaction in certain patients. Further, the stability of Fluosol-type Pluronic F-68-based emulsions is limited; they must be frozen for storage and as manufactured, are not ready for use. Three preparations, the mother emulsion and two annex solutions, must be mixed before the emulsion is suitable for administration.

More generally, the properties and/or biocompatibility of the surfactants known and used so far are still insufficient to allow mastery of these emulsions, notably of their intravascular persistence and stability, and adaptation of their characteristics to a specific therapy. Still more generally, there is a scarcity of substances that are at the same time strongly amphiphilic and surfactive, biocompatible, and industrially feasible, while available at a reasonable cost.

Research has therefore been directed towards developing new surfactants or cosurfactants that are biocompatible and better adapted to the emulsification of fluorocarbons than those in use at present. The fluorinated derivatives of the invention improve such properties as described in U.S. Pat. No. 4,985,550 (Jul. 28, 1987) and U.S. Pat. No. 542,227 (Jun. 22, 1990).

Other fluorinated compounds capable of improving the surfactive properties of fluorinated surfactants are described in U.S. Pat. No. 4,089,804. These compounds are formulated as $(R_F)_nT_mZ$ in which $R_F$ is a perfluoroalkyl chain, n=1 or 2, T is an alkylene, haloalkylene, arylene, alkylenethioalkylene, alkyleneoxyalkylene or alkyleneiminoaklylene chain, m=0, 1 or 2, and Z is a neutral or polar group such as CO—NH—CH$_2$H.

These fluorinated compounds, in association with fluorinated surfactants, can find many applications, but their biocompatibility and toxicity is not assured. Moreover, they must always be used in conjunction with fluorinated surfactants.

Oligomers with perfluoroalkylated terminal groups are also described in EP - A-0 019 584, which can be used as surfactants and as additives in many products, in particular in extinctor foams. These too, then, are not intended for nor adapted to pharmaceutical use.

SUMMARY OF THE INVENTION

The invention provides amphiphilic fluorinated compounds of telomeric structure having the formula of I as described in the Detailed Description. The telomeric compounds comprise a fluorinated alkyl radical, $R_F$, the telogen, linked through an alkylenic group, X, to polymers of taxogens, or polymerizable unsaturated compounds, having the structures of III, a polyhydroxylated group, and V, an amino acid or peptide derivative, also described in the Detailed Description. $R_F$ may be joined as a telogen to a polymer of both III and V, or to a polymer of III alone.

In preferred embodiments, $R_F$ is the radical $F(CF_2)_t$—, wherein t=1 to 10; a preferred linear X is —CH$_2$—CH$_2$—, and a preferred branched X is

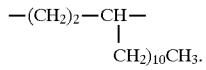

The polyhydroxylated monomers III from which the compounds of the invention are formed have the structure $$-CH_2-CR^1- \quad \text{(III)}$$
$$\begin{array}{c} | \\ CO \\ | \\ NH \\ | \\ R^2 \end{array}$$

and in preferred embodiments, $R^1$ is H or $CH_3$, and $R^2$, the polyhydroxylated group, is $-C(CH_2OH)_3$. In other preferred embodiments, $R^2$ is a glucosyl, galactosyl, or glucaminyl moiety, or is $-Z-R^4-$, wherein Z is a monovalent or bivalent radical selected from the group consisting of $-NH-$, $-(CH_2)_r-N-$ $(R^1)-$, $-(CH_2)_r-O-$, or $(CH_2)_r-S-$, wherein r=2 to 4, and $R^4$ is the lactobionyl, maltosyl or cellobiosyl radical.

The number of polyhydroxylated moieties in the surfactant is n, which can be from 1 to 50; in preferred embodiments, n is from 1 to 20.

The amino acid and peptide derivative monomers V from which the compounds of the invention are formed have the structure:

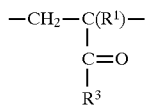

wherein $R^1$ is H or $CH_3$, and $R^3$ is a radical obtained from an amino acid or a peptide by removal of a hydrogen atom from the $NH^2$ group thereof. The number of these amino acid derivative moieties in the surfactant is m, which can be 0 or from 1 to 200. These amino acid structure provide attachment sites for drugs and markers to the surfactant molecules, and in preferred embodiments, m is >1 and a portion of the m moieties are condensed with isothiocyanate to form a fluoresceinated molecule, as in telomer 23 of Example 20. In a preferred embodiment of these fluorescein-labelled surfactant molecules, $R_F$ is $C_8F_{17}$ and X is $-CH_2-CH_2-$.

The invention also provides a method for synthesizing a telomeric compound of the invention wherein n is present and m=0, comprising reacting a monomer having the formula

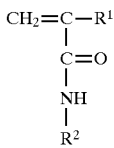

with a telogen of type $R_F-X-SH$, under conditions serving to polymerize said monomer, comprising for example, the presence of a radical forming catalyst, initiator, or promotor, whereby the telomeric compound is formed.

The invention also provides a method for synthesizing a telomeric compound of the invention wherein n is present and m>0, comprising reacting a monomer having the formula

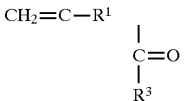

with a telogen of type $R_F-X-SH$, under conditions serving to polymerize said monomer, comprising for example, the presence of a radical forming catalyst, initiator, or promotor, whereby the telomeric compound is formed.

According to another aspect of the invention there are provided formulations comprising any one of the amphiphilic fluorinated telomeric surfactants of the invention. Preferred formulations comprise at least one of these surfactants chemically bound to a biologically active substance or to a marker. The formulations can be in the form of a solution, gel, dispersion, including a liposomal formulation, an emulsion, or a microemulsion. In a particularly preferred embodiment, the amphiphilic fluorinated compound is incorporated into lipid vesicles or liposomes comprising natural or synthetic lipids. The formulations can be manufactured in a form suitable for the transport of gases, as a contrast agent, as a vehicle for the delivery of drugs, or for use as a marker. Formulations and emulsions can further comprise at least one highly fluorinated compound in addition to the amphiphilic fluorinated compound of the invention. In preferred embodiments, the highly fluorinated compound is selected from the group consisting of a bis(F-alkyl) -1,2-ethene; an F-isopropyl-1-F-hexyl-2-ethene; a bis (F-hexyl) -1,2-ethene; perfluorodecalin; perfluoromethydecalin; perfluorodimethydecal in; perfluoromethyladamantene or perfluorodimethyladamantene; a perfluorodi- or tri-methylbicyclo(3,3,1)nonane or a homologue thereof; an ether of the formula $(CF_3)_2CFO(CF_2CF_2)_2OCF(CF_3)_2$; $(CF_3)_2CFO$ $(CF_2CF_2)$ $_3OCF$ $(CF_3)$ 2; $(CF_3)$ $_2CFO$ $(CF_2CF2)_2$ F; $(CF_3)_2CFO$ $(CF_2CF_2)_3F$; F $(CF(CF_3)$ $CF_2O)_2$ $CHFCF_3$; F$(CF(CF_3)CF_2O)_3CHFCH_3$, $(C_6F_{13})_2O,(C_4F_9)_2$ O, an amine selected from the group consisting of $N(C_3F_7)_3$, a perfluoromethylquinolidine or perfluoromethyl-isoquinolidine, a halogenated derivative selected from the group consisting of $C_6F_{13}Br$, $C_6F_{13}CBr_2CH_2Br$, 1-bromo, 4-perfluoroisopropyl cyclohexane, and $C_8F_{16}Br_2$. In particularly preferred embodiments, the highly fluorinated compound is selected from the group consisting of perfluoro-decalin (F-decalin), bis (F-butyl)-1,2-ethene (F-44E) and heptadecafluorobromooctane, $C_8F_{17}Br$ (PFOB). In yet another preferred embodiment, the amphiphilic fluorinated compound is present in a concentration of from about 0.01 to 30% w/v. in an emulsion that further comprises a fluorinated or hydrocarbonated oil phase in a concentration of from about 10 to 125% w/v. The emulsion can further comprise at least a second amphiphilic compound. In preferred embodiments, the second amphiphilic compound is a lecithin or a polyoxyethylene polyoxypropylene copolymer.

DETAILED DESCRIPTION OF THE INVENTION

Figure 1:
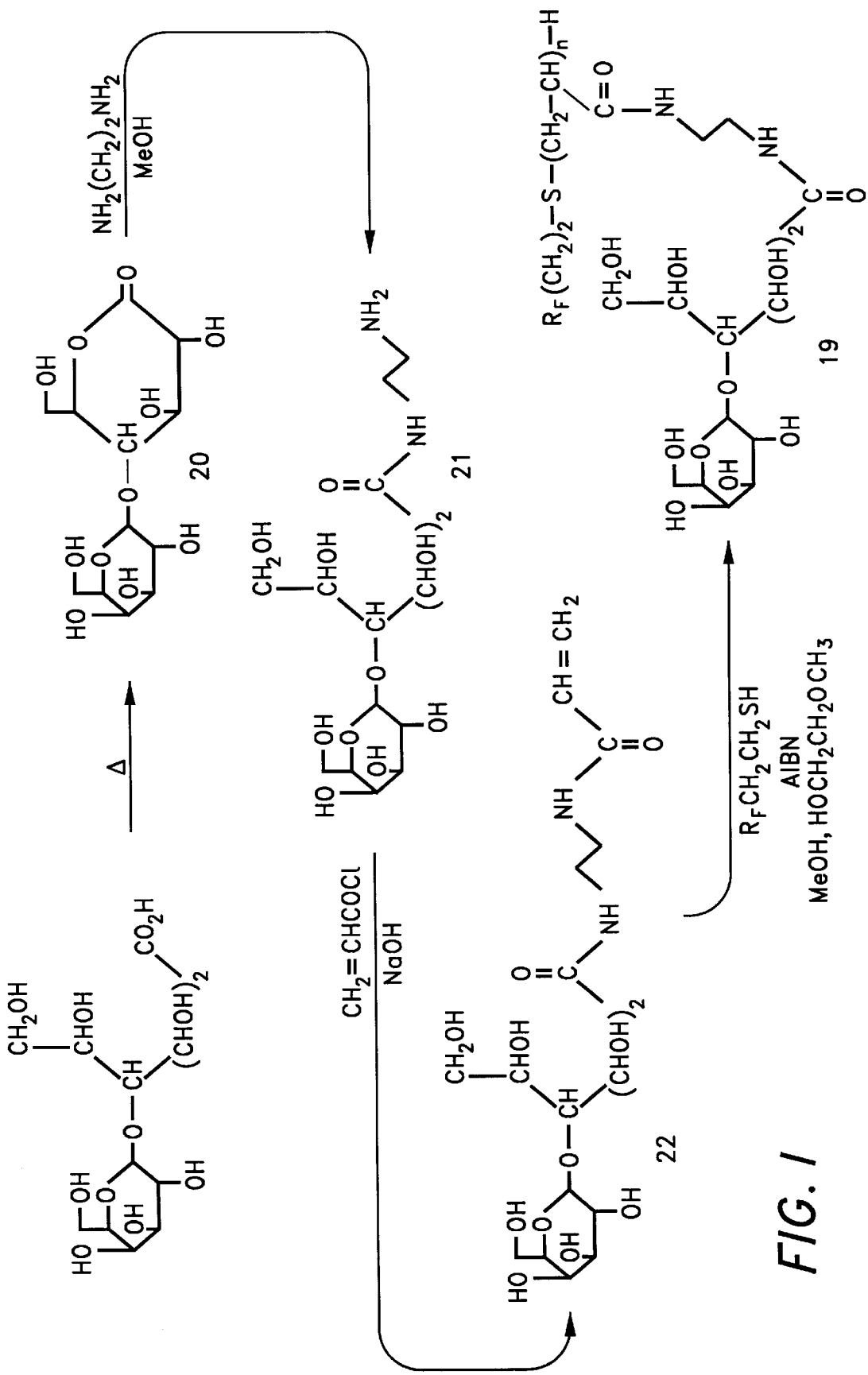
FIG. 1 is a diagram of the synthesis of telomer 19.

The present invention concerns new fluorinated compounds for biomedical use which are biologically compatible and non-toxic, with a very high compatibility with red blood cells and which can be used alone, without the conjunction of other surfactants, whether fluorinated or nonfluorinated.

These fluorinated compounds have the formula:

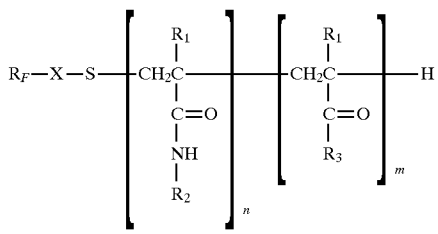

wherein $R_F$ is a fluorinated radical of 4 to 8 carbon atoms; X is a linear or branched $C_{1-24}$ alkylene radical that can further comprise as substitutents one or several moieties selected from the group consisting of —CON(R')—, —SO$_2$N(R')—, —S—, —O— or —N(R')— wherein R' is H or a $C_1$ to $C_{24}$ alkyl radical;

$R^1$ is H or CH$_3$;

$R^2$ is selected from the group consisting of radicals having the formula —(CH$_2$)$_p$—C(CH$_2$OH)$_3$, wherein p equals 0 or is a whole number from 1 to 3, and the radicals of formula —Z—R$^4$, wherein Z is a single valenced or a bivalent radical having the formula —NH—, —(CH$_2$)$_r$—N—(R$^1$)—, or —(CH$_2$)$_r$—O— wherein r equals 2, 3 or 4 and R$^1$ is H or CH$_3$, and R$^4$ is a monovalent radical from an ose, an oside or an amide derivative thereof;

R$^3$ represents a radical derived from an amino acid or a peptide by removing a hydrogen atom from the NH$_2$ group of the amino acid or the peptide;

n is a number from 1 to 50 providing R$^2$ represents —(CH$_2$)$_p$—C(CH$_2$OH)$_3$ when n=1; and m equals 0 or is a number from 1 to 200, provided 0.2<n/n+m<1.

These fluorinated compounds are distinct in bearing both a highly fluorinated, "fluorophilic" end ($R_F$), which has a strong affinity for highly fluorinated or perfluorinated phases, and one or more juxtaposed groups (R$^2$) which are strongly hydrophilic, since they possess several hydroxyl radicals, as for example, R$^2$ representing C(CH$_2$OH)$_3$ or a radical deriving from an ose or an oside.

With these hydroxylated groups, compounds can be obtained presenting both excellent biocompatibility and good surfactive properties, and which are easy to synthesize on an industrial scale.

Thus the fluorinated compounds of the invention are different from those described in documents U.S. Pat. No. 4,089,804 and EP-A- 0 019 584.

Indeed, one of the aspects which distinguish the compounds described in these documents from those of the present invention is that the former do not bear juxtaposed highly hydrophilic groups such as —C(CH$_2$OH)$_3$.

Moreover, the chemical structure of the compounds of these documents was not specifically developed for biomedical use, as is the case of the invention. Indeed, the compounds of U.S. Pat. No. 4,089,804 can be used in such diverse fields as the plastic, rubber, oil, textile, leather, paint, pigment, metal, etc., agriculture and photography industries. The compounds of EP-A-0 019 584 were developed particularly for extinctor foams and for applications requiring dampening and spreading of improved liquids over substrates difficult to moisten or oiled by oil or silicones.

Thus, neither of these documents suggests choosing the hydrophilic, biocompatible end R$^2$ of the invention nor describing any biomedical applications.

According to the invention, the fluorinated radical $R_F$ used is highly fluorinated or perfluorinated, linear or ramified, and may bear in its chain one or more oxygen atoms; certain fluorine atoms of the perfluorinated radical may be replaced by one or more substituents chosen from among the atoms of hydrogen, chlorine or bromine. In this last case, it is preferable that the number of fluorine atoms of the $R_F$ radical be higher than 7, and the substitution is preferably performed at the level of the $R_F$—X bond.

The following radicals are cited as examples of fluorinated $R_F$ radicals that may be used in the invention:

F(CF$_2$)$_t$—, wherein 4≦t≦18;

(CF$_3$)$_2$CF(CF$_2$)$_v$—, wherein 1≦v≦8;

CF$_3$—[CF$_2$CF(CF$_3$)]$_w$—, wherein 1w≦4;

C$_2$F$_5$—[CF$_2$CF(CF$_3$)] —, wherein 1≦ ≦4;

(CF$_3$)$_2$—[CF—CF$_2$CF(CF$_3$)]$_w$—, wherein 1≦w≦4; and

wherein 1≦x≦6 and R$^1_F$ and R$^2_F$, which are identical or different, are chosen from among CF$_3$—, C$_2$F$_5$, n—C$_3$F$_7$—, and CF$_3$CF$_2$CF(CF$_3$)— or in which R$^1_F$ and R$^2_F$ together form a bivalent radical chosen from among —CF$_2$(CF$_2$)$_2$CF$_2$— and —CF$_2$(CF$_2$)$_3$CF$_2$—; CF$_3$(CF$_2$)$_2$O—(CF$_2$CF$_2$O)$_{x8}$—CF(CF$_3$)— with 0≦x$^8$≦6; and CF$_3$(CF$_2$)$_2$O—[CF(CF$_3$) (CF$_2$O)$_{x8}$—CF(CF$_3$)— with 0≦x$^8$≦6.

It is preferable to use a linear fluorinated radical of formula F—(CF$_2$)$_t$ in which t is an even number from 4 to 18.

In the fluorinated compounds of formula (I) of the invention, X is a linear or branched alkylene radical of 1 to 12 carbon atoms which may bear various groups in its chain. For example, X can represent:

—(CH$_2$)$_y$, wherein 1≦y≦12

—(CH$_2$)$_{y1}$—CON(R')—(CH$_2$)$_{y2}$, wherein 1≦y1≦11 and 1≦y2≦11

—(CH$_2$)$_{y1}$—SO$_2$N(R')—(CH$_2$)$_{y2}$, wherein 1≦y11 and 1≦y2≦11

—(CH$_2$)$_{y1}$—S—(CH$_2$)$_{y2}$, wherein 1≦y1≦11 and 1≦y2≦11

—(CH$_2$)$_{y1}$—N(R')—(CH$_2$)$_{y2}$, wherein 1≦y1≦11 and 1≦y2≦11

—CH$_2$—CH$_2$—O]$_{y3}$—CH$_2$—CH$_2$—, wherein 1≦y3≦6

—[CH(CH$_3$)CH$_2$O]$_{y3}$—CH—CH$_2$—,
                                 |
                                 CH$_3$ wherein 1≦y3≦6; and —CHR$^4$ wherein R$^4$ an alkyl radical of 1 to 12 carbon atoms which can comprise one or several double or triple bonds, conjugated or not.

The compounds of the invention also comprise moieties having the structure

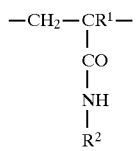

wherein $R^1$ is H or $CH_3$, and $R_2$ is as defined above.

The $R^2$ radicals used in the invention which, in particular, confer better surfactive properties on the fluorinated compounds, are those bearing several hydroxyl groups. Such are the trihydroxymethyl (Tris) radical or those derived from oses, osides or their derivatives, for example their amine derivatives.

Examples of such radicals are those derived from glucose, galactose, mannose, ribose, fructose, maltose, lactose, saccharose, glucosamine, etc.

A radical of $R^2$ derived from oses, osides or their derivatives can be attached to the NH group, either directly or by a bivalent radical of formula $-NH-$, $-(CH_2)_r-N(R^1)-$ or $-(CH_2)_r-O-$ in which r=2, 3, or 4 and $R^1$ is H or $wCH_3$.

Examples of radicals that can be used in the invention are glucosyl, galactosyl and glucaminyl radicals, and radicals of formula $-Z-R^4$ in which Z is as defined above and $R^4$ is the lactobionyl, maltosyl or cellobiosyl radical.

According to the invention, when n>1, the $R^2$ radicals of the various moieties may be different.

The compound of the invention may also comprise moieties having the formula:

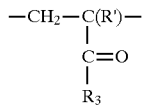

which make it possible to confer other properties on the fluorinated compound, for example the ability to link a drug by a chemical bond to the terminal acid group COOH of the $R^3$ radical, whereby the drug can be released afterwards in a living organism by cleavage of the peptide bond.

With this aim, the $R^3$ group is derived from an amino-acid or a peptide. When $R^3$ derives from an amino acid, its formula is
$-NH-C(R^5)(R^6)-COOH$ in which $R^5$ and $R^6$ correspond to the lateral chain of the amino acid or to a hydrogen atom.

The amino acids used are preferably natural ones such as alanine, valine, leucine, isoleucine, serine, threonine, cysteine, methionine, aspartic acid, glutamic acid, asparagine, glutamine, lysine, glycine, arginine, citrulline, ornithine, phenylalanine, tyrosine, tryptophane, histidine, proline and hydroxyproline. For example, $R^3$ can be a radical derived from glycine or lysine.

According to the invention, $R^3$ can also be derived from a peptide bearing several identical or different aminoacids. As an example of peptides, one can cite that of formula:

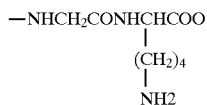

In the fluorinated compounds of the invention, the number, n, of moieties bearing the $R^2$ radical that carries hydroxyl groups can be from 1 to 50. It is preferably from 1 to 20. The number, m, of moieties bearing the $R^3$ radical derived from an amino acid or a peptide can be from 1 to 200, but it is chosen as a function of n to fulfill the following condition: $0.2 \leq n/n+m \leq 1$. When the fluorinated compounds are not intended to be used as a carrier for a marker or a vehicle of drugs, m preferably equals 0.

According to a preferred embodiment of the invention, the fluorinated compound has the formula:

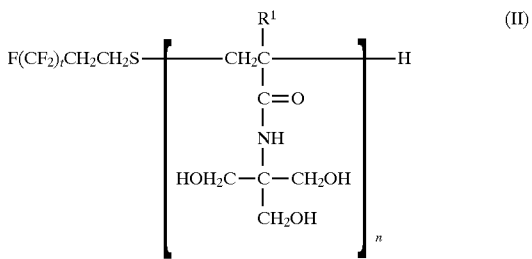

wherein t is an even number from 4 to 10, $R^1$ is H or $CH_3$, and n is a number from 1 to 30.

Double Chain Surfactants:

The invention also includes amphiphilic fluorinated surfactants, having the structure of the example below, wherein X is a branched alkylenic radical bearing an $R_F$ group on one or both branches:

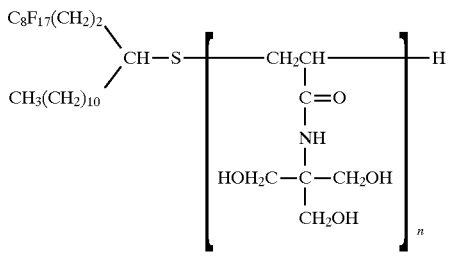

Synthesis:

The fluorinated compounds of the invention can be prepared as follows:

In the case of fluorinated compounds corresponding to the above formula (I), in which m equals 0, these compounds can be prepared by telomerizing monomers of formula:

in which $R^1$ and $R^2$ are as defined above, in the presence of a telogen of formula:

wherein $R_F$ and X are as defined above.

This procedure corresponds to a radicalar telomerization, and consists in the polymerization of monomers of formula (III) in the presence of a strong chain-transfer agent constituted of $R_F-X-SH$ which limits the propagation of the growing macroradical. To the three classical polymerization steps is added the transfer reaction.

In the presence of an efficient transfer agent such as $R_F-X-SH$, the transfer reaction becomes largely preponderant. The size of the telomer so obtained depends on:

1) the constant of transfer (Ct) of the telogen $R_F-X-SH$ to the monomer, which is equal to ktr/kp, i.e., to the ratio of the rate of transfer, ktr, and of the rate of propagation, kp, of the monomer. Indeed, the instantaneous degree of polymerization ($DP_n$) can be deduced from the equation of Mayo, which gives:

$$1/DP_n = Ct \frac{[R_F\text{—}X\text{—}SH]}{[M]}$$

wherein [—$R_F$—X—SH] and [M] represent respectively the instantaneous concentrations in transfer agent (telogen) and in monomer.

2) The initial concentrations in telogen and monomer, thus the relation $R_0$ which equals $[M]_0/[R_F\text{—}X\text{—}SH]_0$ where $[M]_0$ and $[R_F$—X—SH] represent respectively the initial molar concentrations in monomer and in telogen, and 3) to a lesser degree on the concentration in initiator $I_2$.

In the case of perfluorinated thiols, the telogenic agents of the invention, experience shows that their transfer constant (Ct) with respect to the acrylamide-type monomer is close to 0.9. In these conditions, the ratio $R_0$ of the initial molar concentrations allows the prediction of the $DP_n$ of the telomers synthesized thus.

When the base monomer is tris-hydroxymethylacryl amidomethane (TAC) or tris-hydroxymethylmethacrylamidomethane (MTAC), and when the polymerization initiator is $\alpha,\alpha'$-azo-bis-isobutyronitrile (AIBN), previously recrystallized twice in ethanol, the concentrations are calculated in all cases so that $C_O$, the initial ratio of the molar concentration of initiator over the molar concentration of monomer is between $10^{-2}$ and $5\times10^{-2}$.

The telomerization reaction can be carried out in an organic solvent such as methanol or dimethylformamide (DMF) under nitrogen atmosphere. When dimethylformamide is used, the temperature can be maintained at 80° C.

After the reaction, the solvent can be evaporated and the product obtained recovered by classical methods, for example by precipitation.

When the starting monomer is MTAC, as its reactivity is weaker than that of TAC, the formation of weak $DP_n$ telomers is favored, to the detriment of heavier compounds. To avoid this problem, the telogen is added slowly during the telomerization reaction, or the reactants can be added very slowly throughout the progress of the reaction.

To obtain fluorinated compounds of formula (I) in which n=1, an $R_0$ ratio of 1 is used, and they are then purified by chromatography over a silica column.

In the case of fluorinated compounds of formula (II), the above procedure corresponds to the following scheme:

derivative

The fluorinated thiols used as telogens in the procedure of the invention are commercial products, or can be prepared by classical methods, for example by successively treating their halogen (bromine or iodine) homologues with urea and sodium metabisulfite.

The monomers of formula (III) used as starting material in the procedure of the invention can be prepared by classical procedures, for example by reaction of an acrylic or methacrylic acid halide such as acryloyl or methacryloyl chloride with an amine of formula $R^2$—$NH_2$.

When $R^2$ is the $ZR^4$ radical with Z representing —$(CH_2)_r$—N(R'), for example —$(CH_2)_2NH$—, one can start with an ose or an oside bearing a COOH or lactone group which is made to react with a diamine of formula $H_2N$—$(CH_2)_r$—$NH_2$ in the presence or absence of dicyclohexyl carbodiimide. When Z represents NH, hydrazine is used instead of diamine.

When a fluorinated compound of the invention corresponds to the above formula (I) in which m is a whole number from 1 to 200, these compounds can be prepared by an analogous procedure, i.e., by telomerization of the monomers corresponding to the formulas:

and

in which $R^1$, $R^2$, and $R^3$ are as defined above, in the presence of a telogen of formula $R_F$—X—SH in which $R_F$ and X are as defined above.

In this case, the respective concentrations in monomers of formula (III) and formula (V) are chosen as a function of the number of n and m moieties to be included in the fluorinated compound.

The starting monomers corresponding to the formula (V) are commercial products or can be prepared by classical procedures, by the reaction of acryloyl chloride or methacryloyl with the corresponding aminoacid or peptide.

The fluorinated compounds of the invention are advantageous for many applications, as they are strongly amphiphilic. In particular, they are strong surfactants, usually soluble in water, and biocompatible; for example, with no detectable hemolytic action on human red cells, even at concentrations higher than 200 g/L and with a tolerance for some derivatives higher than 4000 mg/kg body weight after intravenous injection in mice. Moreover, drugs or an element or fragment that can serve as marker, can be fixed to them by a chemical bond.

The present invention also includes preparations or formulations for biomedical use having at least one fluorinated compound of formula (I) of the invention. These preparations can be in the form of solutions (including micellar solutions), dispersions such as liposomal formulations, emulsions, and microemulsions, or gels, in water or any other appropriate solvent. In these preparations, the fluorinated compound of the invention can play the part of surfactant, co-surfactant or dispersing agent, or can serve as a vehicle to solubilize or disperse an active principle in the preparation.

Thus the compounds of the invention can be used in pharmacy for the preparation of medicaments in which they play the part of solubilizing, dispersing, or emulsifying agents, for the preparation of solutions or emulsions, administrable orally or parenterally, for example, by injection.

They can be used as surfactants in preparations for pharmaceutical, veterinary or phytosanitary use, and for biological and medical use, containing, in particular fluorocarbon-type oxygen carriers, whose applications include use a blood substitutes, or more generally, for in vivo administration of oxygen.

They can also be used in preparations intended to facilitate diagnosis, in particular by radiography, sonography or nuclear magnetic resonance imaging, or by attaching an appropriate marker or tracer (fluorescein, radioactive markers, for example). In this case, the preparations can be used as contrast agents or markers.

Indeed, the fluorinated compounds of the invention are stronger surfactants than Pluronic F-68, which is presently used in the first commercialized fluorocarbon emulsion for intravascular use, Fluosol-DA (Green Cross Corp., Osaka, Japan).

In these preparations the fluorocarbons or highly fluorinated compounds that serve for the transport of gases such as oxygen can be, for example, linear or cyclic compounds, preferably with molecular weights between 400 and 700, and can be chosen, for example, from the following compounds:

The bis(F-alkyl)-1,2-ethenes and more particularly the bis(F-butyl)-1,2-ethenes, the F-isopropyl-1-F-hexyl-2-ethenes and the bis(F-hexyl)-1,2-ethenes, perfluorodecalin, perfluoromethyldecalin, perfluorodimethyldecalin, perfluoromethyl- and dimethyladamantanes, perfluorodi- and trimethylbicyclo(3,3,1);nonanes and their homologues, the ethers of formula: $(CF_3)_2CFO(CF_2CF_2)_2OCF(CF_3)_2$, $(CF_3)_2CFO(CF_2CF_2)_3OCF (CF_3)_2$, $(CF_3)_2CFO(CF_2CF_2)_2F$, $(CF_3)_2CFO(CF_2CF_2)_3F$, $F[CF(CF_3)CF_2O]_2CHFCF_3$, $F[CF(CF_3)CF_2O]_3CHFCH_3$, $(C_6F_{13})_2O$, $(C_4F_9)_2O$, the amines $N(C_3F_7)_3$, perfluoromethylquinolidines and perfluoromethylisoguinolidines, halogenated derivatives $C_6F_{13}Br$, $C_8F_{17}Br$ (PFOB), $C_6F_{13}CBr_2CH_2Br$, 1-bromo 4-perfluoroisopropyl cyclohexane, $C_8F_{16}Br_2$. These highly fluorinated compounds can be used alone or in mixtures.

In these preparations, solution, emulsions, gels, dispersions, or microemulsions, containing one or several of the highly fluorinated compounds mentioned above, the fluorinated compounds of the invention can be used by associating them with one or several other amphiphilic compounds such as fluorinated or nonfluorinated surfactants. Lecithin is an example of a nonfluorinated surfactant.

The preparations, solutions, gels, dispersions, including liposomal formulations, emulsions, or microemulsions, of the invention are specifically intended to serve as gas carriers, in particular of oxygen, in living medium, for application in human and veterinary medicine and in biology, specifically as blood substitutes, contrast agents for diagnosis, media for treatment of cerebral or cardiac ischemia, for perioperative hemodilution, for the preservation of organs, tissues, embryos, semen, as media to be used in cardiovascular therapy and surgery, for example as cardioplegic or reperfusion solutions or in coronary angioplasty, or as an adjuvant in cancer radiotherapy or chemotherapy, or as drug carriers.

Figure 2:
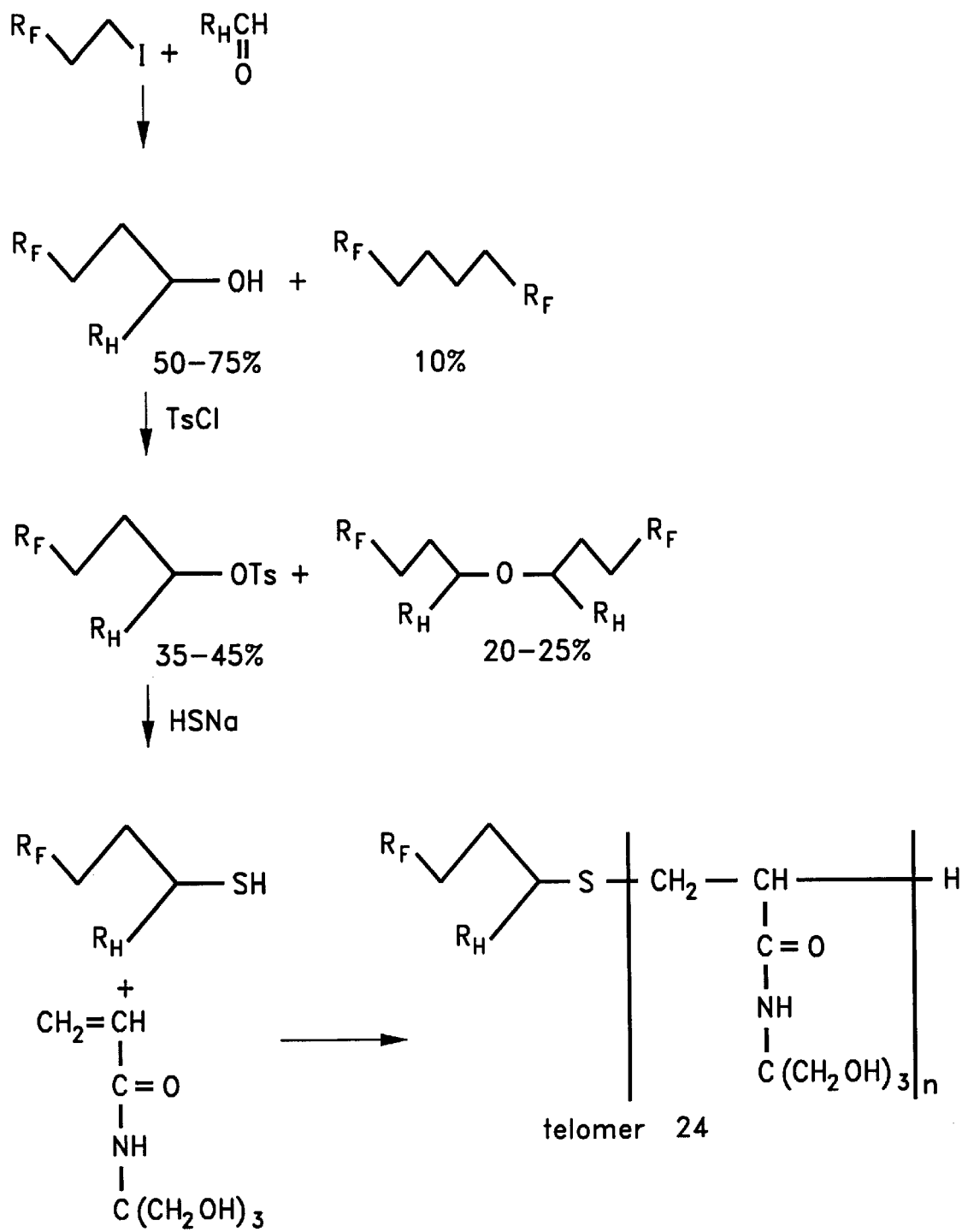
FIG. 2 is a diagram of the synthesis of telomer 24.

Other characteristics and advantages of the invention are more clearly demonstrated by the following examples, which are of course only illustrations, and not intended to be exhaustive. FIGS. 1 and 2 are a schematic flow chart illustrating the synthesis of the telomers 19 and 24, of Examples 19 and 21, respectively.

EXAMPLES

The telomers cited in the following examples correspond in general to the following definition and to FIGS. 1 and 2:

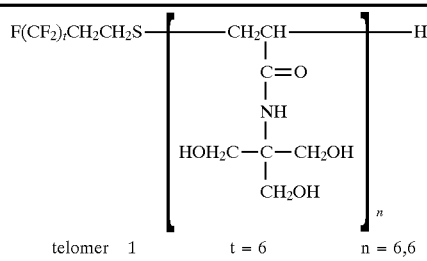

telomer 1    t = 6    n = 6,6

| | | |
|---|---|---|
| 2 | 6 | 4,4 |
| 3 | 6 | 5,4 |
| 4 | 6 | 5,8 |
| 5 | 6 | 10 |
| 6 | 6 | 11,7 |
| 7 | 8 | 3,5 |
| 8 | 8 | 3,75 |
| 9 | 8 | 5,75 |
| 10 | 8 | 5,8 |
| 11 | 8 | 8,2 |
| 12 | 8 | 12,2 |
| 13 | 10 | 6,8 |

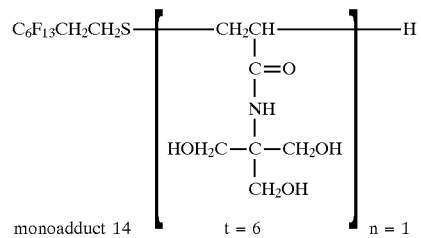

monoadduct 14    t = 6    n = 1

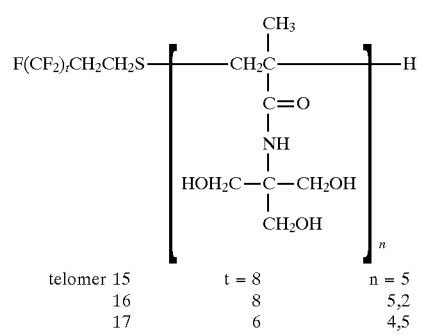

| telomer 15 | t = 8 | n = 5 |
|---|---|---|
| 16 | 8 | 5,2 |
| 17 | 6 | 4,5 |

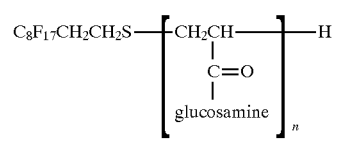

telomer 18    t = 8    n = 5

Example 1:
A—Preparation of trihydroxymethylacrylamido-methane (Trisacryl or TAC)

30 g of trihydroxymethylacrylamidomethane (0.25M) are dissolved in 100 mL of a 0.1M NaOH solution in the presence of 200 mg of $NaNO_2$ (inhibitor of polymerization). The vigorously stirred solution is cooled under nitrogen at 0° C. Then acryloyl chloride (34 mL; 0.375M) is added dropwise over a period of three hours. During this addition the pH of the solution is maintained at 11–12 by addition of NaOH solution (3M).

After 3 h stirring at 0° C., the reaction is continued for 12 h at room temperature, the pH being controlled regularly and maintained at 11–12. The solution is then acidified to pH 3 to 4 with HCl 4N, extracted with ether, and concentrated to a volume of 50 mL. The liquor is poured into 300 mL of ethanol, in which the greater part of the salts precipitate. The filtrates are then concentrated and the residue is flash-chromatographed over a short silica column (eluent AcOEt/MeOH 8/2).

The trisacryl crystallizes in methanol. 29 g of trihydroxymethylacrylamidomethane are recovered (yield 67%)F 140° C. (Lit.: 131°–133° C.). The $^{13}C$ and $^1H$ NMR spectra conform to the expected structure.

B - Synthesis of telomer 1

Into 100 mL of methanol, 8.75 g (0.05M) of the trisacryl monomer are introduced, and the solution is brought to 40°–50° C. When the trisacryl is entirely dissolved, 3.8 g of perfluoro 1H,1H,2H,2H octanethiol (0.01M, i.e., $R_0=5$) and 87 mg of AIBN are introduced. The solution is then brought to reflux under nitrogen atmosphere. The progress of the reaction is followed by CCM (Rf trisacryl=0.75, eluent AcOEt/MeOH). After 12 h reaction, additional AlBN (73 mg) is added. After 24 h of ebullition, the trisacryl has entirely disappeared. The solvent is evaporated under reduced pressure, until a volume of 30 mL is obtained. The liquor is poured dropwise into 200 mL of anhydrous ether under vigorous stirring.

The white precipitate obtained is filtered, 200 mL of ether are added and the mixture is stirred at room temperature and again filtered. After washing with anhydrous ether, the telomers are dried under reduced pressure. 10 g of product 1 (yield 80%) are recovered.

After drying or lyophilization, $^1$H NMR in DMSO d6 analysis of the telomer gives the $DP_n$ of the macromolecule, by comparison of the area of the signal due to the methylene in 1 of the octanoyl chain at $\delta=2.75$ with those due to the amide protons NH at $\delta=7.4$.

$$DP_n=INH.\times 2/ICH_2$$

$DP_n$ is thus found to be 6.6.

Elemental analysis: % C 42.18; % H 5.81; % N 6.34; % F 16.77. The elemental analysis of the fluorine also gives the $DP_n$: $DP_n=(247/\% \text{ F}-380) (1/175)-6,94$.

Example 2–Example 13

Products 2–13 (see Table I) are prepared according to the procedure of Example 1.

In Table 1: MTrs, MC10F21C2H4SH, MC8F17C2H4SH or MC6F13C2H4SH, MAIBN, MTelo represent respectively the weights in grams of the trisacryl, perfluoro 1H, 1H, 2H, 2H, dodeca, deca or octanethiol, α,α' azobis isobutyronitrile reactants and of telomers obtained. $VCH_3OH$ represents the volume of methanol employed in the reaction.

silica column (eluent AcOEt then AcOEt/MeOH 8/2). 2.33 g (yield 42%) of monoadduct and 1.92 g of a mixture of telomers with higher $DP_n$ (di- and triadduct) are isolated. The monoadduct (F=100° C.—Hex/AcOEt) is soluble in organic solvents such as AcOEt, $CH_3CN$, $CH_3OH$, $CHCl_3$, insoluble in water.

Monoadduct:
— $^1$H RMN ($\delta$ ppm, DMSO d6): 7,3(s,1H,NH); 4,75(t, 3H, OH); 3,59(d, 6H, $CH_2$); 2,78(m, 4H, $(CH_2)_2$ α to the sulfur); 2,45(m, 4H, $(CH_2)_2$.
$^{13}$C RMN($\delta$ ppm, DMSO d6): 171,82 (CO); 120–100 (C RF); 62,45 ($C(CH_2OH)_3$); 60,7($3CH_2OH$); 36,11 ($COCH_2$); 31,12 (t, $CH_2$ α to $C_6F_{13}$); 27,11 ($CH_2S$); 21,76 (t, $CH_2$ β to $C_6F_{13}$).

Example 15

A-Synthesis of trihydroxymethylmethacrylamidomethane (MTAC)

The preparation procedure for the monomer is analogous to that of the trisacryl monomer (Example 1-A). The product crystallizes in methanol (F=98° C.; Lit. 93°–94° C.). The yield is 45%.

B-synthesis of telomer 15

Into 50 mL of methanol, MTAC (4.72 g; 0.025M) is introduced, and the solution is brought to ebullition. Perfluoro 1H,1H,2H,2H decanethiol (400 mg) in methanol (10 mL), then AIBN (50 mg) are added. After 1 hr reaction, perfluoro 1H,1H,2H,2H decanethiol (2 g) and AlBn (100 mg) in methanol (20 mL) are added in small fractions. The solution is then maintained at ebullition until the monomer has totally disappeared (24 h). The solvent is then evaporated to a liquor. This is poured dropwise into 200 mL of anhydrous ether. The white precipitate obtained is filtered, dissolved in 100 mL of anhydrous ether, stirred at room temperature and again filtered. After washing with anhydrous ether, the telomers are dried under reduced pressure, then dried. Telomer 15 (3.91 g; yield 55%) is thus recovered.

$^1$H NMR analysis in DMSO $d^6$ in the same conditions as above given a $DP_n$ of 5.

Evaporation of the precipitation solvents gives a mixture of telomers of low $DP_n$ rich in monoadduct (Table II).

TABLE I

Preparation Conditions for Products 1–13:

| Product | MTrs | $MC_6F_{13}$ | $MC_8F_{17}$ | $MC_{10}F_{21}$ | Ro | MAIBN | $VCH_3OH$ | MTeio | Rdt | $DP_n$ |
|---|---|---|---|---|---|---|---|---|---|---|
| 1 | 8,75 | 3,8 | | | 5 | 0,16 | 100 | 10 | 80 | 6,6 |
| 2 | 3,5 | 2,17 | | | 3,5 | 0,16 | 50 | 3,55 | 63 | 4,4 |
| 3 | 3,5 | 1,9 | | | 4 | 0,16 | 50 | 3,94 | 73 | 5,4 |
| 4 | 11 | 4,77 | | | 5 | 0,2 | 100 | 12,5 | 79,5 | 5,8 |
| 5 | 3,5 | 1,27 | | | 6 | 0,16 | 50 | 3,86 | 81 | 10 |
| 6 | 1,75 | 0,63 | | | 6 | 0,06 | 30 | 1,98 | 83 | 11,7 |
| 7 | 8,75 | | 8 | | 3 | 0,23 | 100 | 11,05 | 66 | 3,5 |
| 8 | 2,18 | | 3 | | 2 | 0,115 | 50 | 3,07 | 59 | 3,75 |
| 9 | 4,37 | | 2,99 | | 4,0 | 0,115 | 50 | 5,2 | 71 | 5,75 |
| 10 | 11 | | 6,03 | | 5 | 0,16 | 100 | 13,2 | 77,5 | 5,8 |
| 11 | 4,37 | | 3 | | 5,5 | 0,05 | 50 | 5,74 | 78 | 8,2 |
| 12 | 2,18 | | 1 | | 6 | 0,115 | 50 | 2,66 | 82 | 12,2 |
| 13 | 14 | | | 7,73 | 6 | 0,2 | 100 | 18,7 | 86 | 6,8 |

Example 14

Synthesis of the monoadduct: N-[(trihydroxymethyl) methyl] 4-thia-6-(n-perfluorohexyl) hezanamide, 14

Trisacryl (1.75 g, $10^{-2}$M), perfluoro 1H,1H,2H,2H octanethiol (3.8 g) and AIBN (100 mg) are dissolved in 30 mL of methanol and brought to ebullition under nitrogen atmosphere for 12 h. The solution is then concentrated under reduced pressure. The residue is chromatographed over Examples 16–17

The method described for preparing compound 15, with variation of the Ro ratio gives products 16 and 17 (Table II).

TABLE II

Preparation conditions for products 15–17

| Product | MTAC | MC$_8$F$_{17}$C$_2$H$_4$ | MC$_8$F$_{13}$C$_2$H$_4$ | Ro | MAIBN | VCH$_3$OH | MTeio | Rdlt | DP$_n$ |
|---|---|---|---|---|---|---|---|---|---|
| 15 | 4,72 | 2,4 | | 5 | 0,15 | 80 | 3,91 | 55 | 5 |
| 16 | 9,45 | 4,8 | | 5 | 0,2 | 110 | 8,2 | 57 | 2,5 |
| 17 | 9,45 | | 3,8 | 4,5 | 0,2 | 120 | 6,9 | 52 | 5,4 |

Example 18

A—2 acrylamido—2 deoxy-D-glucose

The preparation uses the techniques proposed by J. KLEIN and D. HERZOG (Makromol. Chem. 188, 1217 (1987)).

B—Synthesis of telomer 18

The telomers of acryloylglucosamine are prepared according to the above protocol.

Acryloylglucosamine (2.3 g; 0.01M) is introduced into 75 mL of anhydrous methanol. The vigorously stirred solution is brought to 40°–50° C. under nitrogen atmosphere. At total dissolution, perfluoro 1H,1H,2H,2H (1.05 g), decane thiol (Ro=4.6) and AlBN (120 mg) are added, and the solution is brought to ebullition. The progress of the reaction is followed by CCM. After 8 h, AlBn (50 mg) is again added. After 24 h of ebullition the reaction is complete. The solution is concentrated to half under reduced pressure, then poured dropwise into 250 mL of ether. After 1/2 h stirring, the precipitate is filtered, dissolved in 200 mL of ether, stirred again for ½ h, then filtered and dried under reduced pressure. After drying, the product 18 (2.7 g; yield 80%) is recovered. The DP$_n$ is shown by $^1$H NMR in DMSO d$^6$ by comparison of the areas of the signals due to CH$_2$S of the perfluorinated chain at δ=2.7 with those of the NH (δ=7.5) or anomeric OH (δ=6.5) of the n glucosamide moieties.

$$DP_n = \frac{ICH_2 \times 2}{IOH_1} = 5$$

The water-solubility of the telomer obtained is higher than 200 g/L. CMC:=1.6×10$^{-4}$ M/L

Example 19

Synthesis of telomer 19

This example illustrates the preparation of telomer 19 (FIG. 1), i.e., the products corresponding to formula (I) in which R$_2$ is the group —(CH$_2$)$_2$—NH—C(O)—(CHOH)$_2$—CH(CHOH—CH$_2$OH)-glucosyl.

Lactobionolactone 20 is obtained quantitatively from lactobionic acid by dissolution then repeated concentration under reduced pressure of lactobionic acid in 2-methoxy ethanol. Slow addition of lactobionolactone in a large excess (5/1) of ethylenediamine in solution in methanol gives lactobionamide 21 in quantitative yield after 2 h of ebullition. The crystallized product obtained is then condensed with acryloyl chloride in a aqueous NaOH solution giving product 22. After purification by chromatography over silica column (eluent AcOEt/MeOH/H$_2$O), telomerization is realized in the usual conditions in a mixture of methanol and methoxy ethanol under nitrogen atmosphere.

When hydrazine is used in the place of ethylenediamine the reaction takes place in the same conditions.

Example 20

Synthesis of telomer 23:

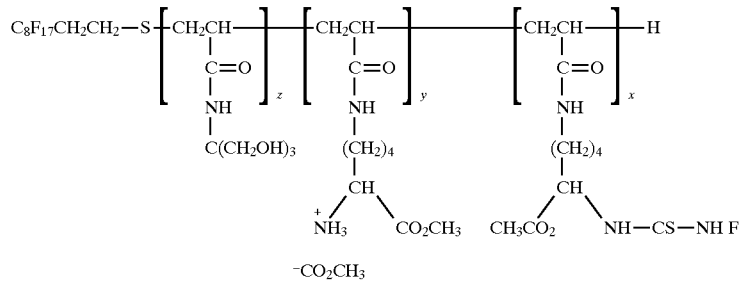

x=0.33, y=0.35, Z=6.3, F=fluoroscein

1-Synthesis of N-tbutyloxycarbonyl-N-ε(acryloyl)-L-methyl lysinate

Into a 250 mL reactor are introduced under inert atmosphere 4 g (13.5 mM) of BocLys(AcOH)OMe, 100 mL of CH$_2$Cl$_2$ and 5 mL of diethylisopropylamine. To this solution, under vigorous stirring and cooling to 0° C., acryloyl chloride (1.3 mL, 20.3 mM), diluted in 10 mL of CH$_2$Cl$_2$, is added dropwise. After 4 h reaction at 0° the solution is diluted with 50 mL of CH$_2$Cl$_2$, washed with 100 mL of HCl 1M, H$_2$O, and dried over sodium sulfate. The solvents are evaporated and the oily residue chromatographed over silica column (eluent AcOEt/hexane 1/1). Pure Boc Lys(Acr)OMe (3.5 g, Yield 88%) is recovered in the form of an oil: Rf (AcOEt/Hexane)=0.45, (α$_D$)=+7.5° (c, 1, CHCl$_3$).

1H NMR (CDCl$_3$) : 6.29 (1H, d, J=15.3 Hz, vinyl), 6.11 (1H, dd, J$_1$=15.3 Hz, J$_2$=10 Hz, vinyl), 5.96 (1H, m, NH), 5.62 (1H, d, J=10 Hz, vinyl), 5.15( (d, 1H, J=7.7 Hz, NH, 4.27 (1H, m, CH$_2$), 3.74 (2H, s, OMe), 3.22 (2H, td, CH$_2$), 1.85 (2H, m, CH$_2$β), 1.6 (4H, m CH$_2$ λ, δ), 1.44 (9H, s, tBu).

13C NMR (CDCl$_3$) : 172.23, 167.71, 130.96, 126.23, 80.00, 60.39, 53.42, 53.2, 52.29, 39.14, 32.47, 26.93, 22.62, 21.03, 14.21.

2-synthesis of cotelomer Boc Lys(Acr)OMe+Trisacryl

In 100 mL of degassed anhydrous methanol are dissolved 1.3 g (4.1 mM) of BocLys(Acr)OMe, 4.35 g (24.8 mM) of tris(hydroxymethyl)-acrylamidomethane trisacryl and 2.31 g (4.8 mM) of perfluorodecanethiol 1H,1H,2H,2H. The solution is brought to ebullition under argon and stirring, and α,α'-azobisisobutyronitrile (AIBN, 100 g) is added. The solution is maintained at ebullition until the monomers are totally consumed (16 h), then concentrated until a liquor is obtained; this is poured dropwise into 200 mL of anhydrous ether maintained under stirring. The white precipitate thus obtained is filtered, 200 mL of ether are added, and the mixture is stirred for 30 mn and again filtered. After drying and lyophilization, an amorphous white powder (6.1 g, yield 77%) is obtained. The degree of polymerization and the composition of the telomer are determined as above by $^1$H NMR in DMSO d6. The $DP_n$ is about 7, i.e., 6.3 THAM moiety for 0.78 lysine ones.

$^{13}$C NMR (DMSO d$^6$): 125–105 (CF$_2$), 78.54 (C of tBu), 62.55 (C of THAM), 60.9 (CH$_2$OH, THAM), 28.42 (tBu).
$^{19}$F NMR (DMSO d$^6$): −79.89 (t), −113, −121.18, −122,−122.29,−125.33.

3-Hydrolysis of the t-butyloxycarbonyl functions 6 g of the above telomer are dissolved in 20 mL of a solution of CF$_3$CO$_2$H and CH$_2$Cl$_2$ (50/50 v/v). After 2 h stirring under inert atmosphere at room temperature, the solution is concentrated under reduced pressure. The oily residue is then ground in anhydrous ether and the precipitate obtained is filtered and rinsed abundantly with ether. After drying and lyophilization, the hydrolysis of the t-butyloxycarbonyl group is confirmed, by $^1$H NMR (DMSO d$^6$), by the disappearance of the signal at δ=43 ppm.

4-Condensation of the isothiocyanate of fluorescein

Into 20 mL of pyridine are introduced 3 g (1.6 mM) of the preceding telomer and 0.5 g (1.3 mM) of fluorescein isothiocyanate. After 12 h stirring at room temperature, the solvent is evaporated under reduced pressure and the residue is chromatographed over a Sephadex® column LH60 (eluent MeOH). The product, which is fluorescent, no longer contains any free fluorescein visible by CCM. After lyophilization, $^1$H NMR shows that condensation has taken place yielding 50%. The composition of the telomer is thus x=0.33 (fluorescein), y=0.35 (NH$_3$+,CH$_3$CO$_2$—), z=6.3. UV (H$_2$O): λ max=458,486 nm.

Example 21
Synthesis of telomer 24:

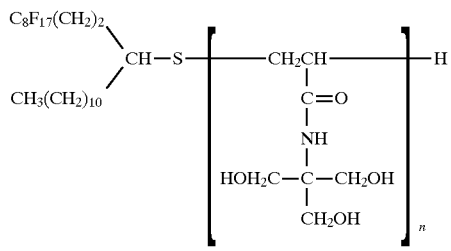

The synthesis of this variety of molecules can be effectuated by reacting the fluorinated thiol with either the trisacryl moiety or with the acetylated trisacryl moiety. An example is illustrated in FIG. 2.

1. synthesis of tris(hydroxymethyl)-acrylamidomethane

This synthesis was conducted as described previously in Example 1A.

2. Synthesis of 1-[(2-F-octyl)ethyl]dodecyl thiol
2.1 Synthesis of 1-[(2-F-octyl)ethyl]dodecanol A solution of 2(F-octyl)ethyl iodide (45.9 g, 0.080M) in dry ether (150 mL) was added dropwise over 2 hours to dry magnesium (2.5 g, 0.1M) in 10 ml of dry ether under reflux. The reaction was initiated by addition of a catalytic amount of iodine. The mixture was then refluxed for 0.5 h.

After cooling, dodecyl aldehyde (14.3 mL, 11.9 g, 0.065 M) in dry ether (150 mL) was added dropwise and the mixture was refluxed overnight.

After cooling, the mixture was hydrolyzed with 10% aqueous ammonium chloride solution. The organic layer was then filtered over Celite 545, washed with a dilute hydrochloric acid solution (1×300 mL), water (4×300 ml), and dried over Na$_2$SO$_4$.

The crude product was purified by column chromatography on silica gel. Hexane was used to remove the by-product of Wurtz' duplication (1.0 g, 2%) followed by (Hex/AcOEt 4:1) to isolate the desired product which was recrystallized in hexane (25.8 g, 63%).

Tlc (Hex/AcOEt 9:1): R$_f$=0.4.
F=86° C.
$^1$H-NMR (CDCl$_3$, 45° C.): 0.90 (t, $^3$JC,H=6.2 Hz, 3H, CH$_3$), 1.30 [s, 16H, (CH$_2$)$_8$], 1.50 [m, 4H, (CH$_2$)$_2$], 1.75 [m, 2H, (CH$_2$)$_9$—CH$_2$—CH—OH], 2.25 (m, 2H, CH$_2$—CH$_2$—C$_8$F$_{17}$), 3.70 (m, 1H, CH—OH). $^{13}$C—NMR (CDCl$_3$, 45° C.): 12.9 (CH$_3$), 21.9 (C$_{10}$), 25.1 (C$_9$), 26.8 (t, $^2$JC,F=22.1 Hz, CH$_2$—C$_8$F$_{17}$), 27.0 (CH$_2$—CH$_2$—C$_8$F$_{17}$), 28.7 (C$_8$), 29.0 [m, (CH$_2$)$_5$], 29.1 (C$_7$ to SH), 68.9$^4$ (CH—OH), 37.2 (Cα to SH).

2.2 Synthesis of 1-[(2-F-octyl)ethyl]dodecyl tosylate 6.5 g of tosylchloride (34 mM) were added slowly over a 3-day period to a solution of 6 g of 1-[(2-F-octyl)ethyl]dodecanol (0° C., 9.5 mN) in 120 mL of dry pyridine.

After acidification with 300 mL of H$_2$SO$_4$ 5N, an extraction was effected in ether. The solution was then washed with iced water, dried on Na$_2$SO$_4$, filtered, concentrated, and separated on a silica column with heptane. Then (heptane/AcOEt:10/1) gave the corresponding tosylate (2.5 g, 33%).

F=27° C. $^{13}$C NMR : 14.1(CH$_3$), 21.5(CH$_3$ arom), 22.8 (C10), 24.8 (C9), 25.1 (t, CH$_2$ β to RF), 26.8 (t, CH$_2$ α to RF), 29.5 [m, (CH$_2$)6], 32.0 (C2), 34.5 (Cl), 82.2 (CH-OTs), 127.8–129.9 (2CH2 arom).

2.3 Synthesis of 1-[(2-F-octyl)ethyl]dodecyl thiol 0.8 g (14.3 mM) of sodium hydrosulfite hydrate (HSNa) were mixed and 4.8 g (6.1 mmol) of 1-[(2-F-octyl)ethyl]dodecyl tosylate were dissolved in 120 ml of dry DMF. The mixture was stirred at room temperature for 2–3 days, and the progress of the reaction was monitored by TLC (AcOEt/hexane 9:1). Tie solvent was removed under reduced pressure at 60° C.

The residue was then dissolved in 150 mL of ether. After filtration for the elimination of sodium tosylate, the organic phase was washed with water (5×150 ml) and dried over Na$_2$SO$_4$.

The crude product was purified by column chromatography on silica gel with hexane. (liquid, 3.2 g, 80%). $^{13}$C NMR (CDCl$_3$: 14.1 (CH$_3$), 22.8 (C10), 24.8 (t, 2JCF=22 Hz, α to RF), 27.1 (t, 3JCF=2.6 HZ, β to RF), 29.5 [m, (CH$_2$)$_7$], 32.0 (C$_γ$ to SH), 34.2 (Cβ to SH), 51.6 (CH—SH).

Example 22
Stability of trihydroxymethylacrylamidomethane-type telomers in sterilization conditions 1 g of TACC$_8$F$_{17}$C$_2$H$_4$ (DP$_n$=5, M=1355) is dissolved in 100 mL of distilled water. Fractions of 10 mL of this solution are distributed into a series of flasks containing 20 mL, which are then hermetically closed. At instant t=0 the solutions are placed in an autoclave maintained at 125° C. and at times t=15 mn, 30 mn, 1 h, 2 h, and 4 h, one of the samples is removed, cooled to room temperature then frozen at −30° C. for lyophilization. After lyophilization the residue is dissolved in 0.5 mL of DMSO and analyzed by $^1$H NMR (DMSO d6).

Whatever the time t, no evolution in the aspect of the solutions is observed. The $^1$H NMR spectra are identical in all ways to those realized before sterilization. The same result was observed with the telomer 23. Thus sterilization causes no degradation in this type of telomer.

Example 23

Toxicity in cell cultures

The toxicity of products 3 and 4 was determined on lymphoblastoid cell cultures of the Namalva type, which grow in an RMPI medium containing 10% of serum of veal foetus at 37° C. under 7% of $CO_2$ following the method described by M. Le Blanc., J. G. Riess, D. Poggi and R. Follana in *Pharm. Res.* 195 (1988). The results are presented in Table III.

TABLE III

Toxicity in cell cultures

| Product | Concentration g/l | mM/l | Results % of growth and viability with regards to reference |
|---|---|---|---|
| 3 | 10 | 7,5 | 16/73 |
|  | 5 | 3,8 | 46/96 |
|  | 1 | 0,75 | 71/104 |
| 9 | 10 | 6,7 | 29/67 |
|  | 5 | 3,3 | 77/97 |
|  | 1 | 0,67 | 80/100 |

It is concluded that even at a concentration of 10 g/L, solutions of 3 and 9 have little effect on these cell cultures despite their strong surface tension.

Example 24

Hemolytic activity

The hemolytic activity of products 3, 9, and 15 is determined by adding 2 mL of a solution of 3 at 200 g/L in physiological water to an equal volume of a suspension of human erythrocytes at 1% in an isotonic phosphate buffer. After 1 h of incubation at 37° C. the solutions are centrifuged in order to precipitate the unhemolyzed cells. The degree of hemolysis is determined by spectrophotometric measurement (540 nm) in comparing the quantity of hemoglobin liberated in the supernatant in the presence of 3 with the quantity liberated by two reference samples, 0% (NaCl 9%) and 100% ($H_2O$). The percentage of hemolysis is calculated according to: t of hemolysis=100 ($DO_{test}$–$DO_{NaCl}$). The results are presented in Table IV.

TABLE IV

Hemolytic Activity of Perfluoroalkylated Telomers

| Product | Initial Concentration g/l | mM/l | Hemolysis Visual | % |
|---|---|---|---|---|
| 3 | 200 | 150,9 | 0 | 0 |
| 9 | 200 | 133,3 | 0 | 0 |
| 15 | 200 | 140,4 | 0 | 0 |
| NaCl |  |  | 0 | 0 |
| $H_2O$ |  |  | ++++ | 100 |

The absence of hemolysis at these strong concentrations in products 3, 9 or 15 is particularly remarkable.

Example 25

Toxicity in vivo in mice

The in vivo toxicity of compound 3 was studied by practicing on 10 mice a rapid intravenous injection (caudal vein) of 0.5 mL (25 mL/kg in weight of animal) of a solution of this product in physiological water (see Table V).

TABLE V

Results of in vivo toxicity tests on mice

| Product | Concentration g/l | mg/kg | Survival/10 |
|---|---|---|---|
| 3 | 75 | 1875 | 10 |
|  | 100 | 3950 | 9 |
| 9 | 75 | 1875 | 10 |
|  | 100 | 2400 | 4 |

Example 26

Surface activity

The surface tension, $\gamma_s$, of an aqueous solution of telomer 9 was determined at different concentrations, as was the interfacial tension, $\gamma_1$, between this solution and two fluorocarbons: F-decalin and F-octyl bromide (Table VI).

TABLE VI

Surface Activity of Perfluoroalkylated Telomer 9 Compared with that of Pluronic F-68

| Product | Concentration (g/l) | $\gamma_s^a$ | $\gamma_1/FDC^a$ | $\gamma_1/PFOB^a$ |
|---|---|---|---|---|
| 9 | 1 | 35,5 | 14,1 | 11,8 |
|  | 0,1 | 32,2 | 12,9 | 10,9 |
|  | 0,01 | 39,3 | 22,8 | 20,1 |

EXAMPLE 27

Determination of the CMC

The critical micellar concentrations are measured according to the process described by Menger and Portnoy, *J. Am. Chem. Soc.* 89. 4698 (1967) (Table VII).

TABLE VII

Critical Micellar Concentrations of Telomers 1–17

| Product | TAC | MTAC | $DP_n$ | M | CMC mM/l |
|---|---|---|---|---|---|
| 1 | C6F13C2H4 |  | 6,6 | 1535 | 0,33 ± 0,05 |
| 2 | C6F13C2H4 |  | 4,4 | 1150 | 0,35 ± 0.05 |
| 3 | C6F13C2H4 |  | 5,4 | 1325 | 0,33 ± 0.05 |
| 6 | C6F13C2H4 |  | 11,7 | 2430 | 0,35 ± 0,05 |
| 7 | C8F17C2H4 |  | 3,5 | 1090 | 0,033 ± 0,005 |
| 9 | C8F17C2H4 |  | 5,75 | 1485 | 0,033 ± 0,005 |
| 11 | C8F17C2H4 |  | 8,2 | 1925 | 0,03 ± 0,005 |
| 12 | C8F17C2H4 |  | 12,2 | 2610 | 0,035 ± 0,005 |
| 13 | C10F21C2H4 |  | 6,8 | 1770 | 0,005 ± 0,0005 |
| 15 |  | C8F17C2H4 | 5 | 1425 | 0,027 ± 0,510$^{-5}$ |
| 17 |  | C6F13C2H4 | 4,5 | 1230 | 0,23 ± 0,05.10$^{-5}$ |

The CMC of the TAC C8F17C2H4 is 3 10$^{-5}$ M/L; it is 10 times higher for the TAC C6F13C2H4.

EMULSIFICATION PROPERTIES

Perfluorodecalin (FDC) emulsions are prepared either by sonication or by mechanical microfluidization under high pressure. Various formulations have been prepared. The emulsions obtained were compared with FDC/Pluronic F-68 emulsions.

It always required less energy to make an emulsion with the TAC-type surfactants than with Pluronic F-68. There is also a stronger stabilizing power during the aging of the emulsions at 4°, 25°, 40° and 50° C.

EXAMPLE 28

Emulsions Prepared by Sonication

Sonication is effected by a BRANSON B 30 sonicator in pulsed mode with a 3 mm diameter probe. The probe is placed at the interface. The aging of the emulsion is followed by measuring the average size of the particles by the photosedimentation method at J0, J3, J7, etc. at 4°, 25° and 50°±1° C.

The sonication time needed is only half of that required for an emulsion prepared with Pluronic F-68. The emulsion prepared with product 9 presents, after 3 months, a relative percentage of growth of the average size of the particles 8 times smaller at 4° C. and 5 times smaller at 25° C. compared to the reference sample (FDC/Pluronic F-68, 50/3% p.v). Moreover, this emulsion remains stable after 70 days at 50° C., while under the same conditions the emulsion prepared with Pluronic F-68 is broken after 55 days (see Table VIII).

After addition of Ampicillin (5 mg/L) and sodium azide (200 mg/L), the emulsions are stored at −4°, 25° and 50° C. in sterile flasks. The emulsions prepared with surfactant 3 are more stable than those containing Pluronic F-68, no matter what the temperature of storage (Table IX).

70 mL of an emulsion of FDC/surfactant (100/4.5% weight per volume) is obtained by adding 33.9 mL of a solution of product 3 to 36.1 mL of FDC. After 7 min preemulsification, the best distribution is obtained with the microfluidizer after 20 passes. An emulsion of the same formulation is prepared with Pluronic F-68.

TABLE VIII

Stability of Emulsions made by Sonication

| Composition of the Emulsion % FDC p/v/ surfactant (% p/v) | Preparation Conditions power | Preparation Conditions time(mn) | After Preparation $J_0$ | Average Diameter of Particles after 3 months ($\mu$m) 4° C. | Average Diameter of Particles after 3 months ($\mu$m) 25° C. | Average Diameter of Particles after 3 months ($\mu$m) 50° C. | % of relative growth 4° C. | % of relative growth 25° C. |
|---|---|---|---|---|---|---|---|---|
| 50/9(3%) | 7 | 5 | 0,30 | 0,49 | 0,68 | 1,51[a] | 63 | 127 |
| 50/Pluronic F-68(3%) | 7 | 10 | 0,23 | 1,34 | 1,59 | broken & $J_{55}$ | 483 | 591 |

[a]measured at $J_{70}$.

TABLE IX

Results of emulsions prepared with the Microfluidizer

| Composition of the Emulsion % FDC p/v/ surfactant (% p/v) | Number of passes | after preparation J* | average diameter ($\mu$m) after 2 months 4° C. | average diameter ($\mu$m) after 2 months 25° C. | average diameter ($\mu$m) after 2 months 50° C. | relative % of growth 4° C. | relative % of growth 25° C. | relative % of growth 50° C. |
|---|---|---|---|---|---|---|---|---|
| 100/Pluronic F-68(4,5%). | 30 | 0,16 | 1,41 | 1,65 | 2,36 | 780 | 930 | 1680 |
| 100/3(4,5%) | 20 | 0,16 | 0,44 | 0,87 | 1,90 | 175 | 444 | 1088 |

Example 29

Emulsions prepared by microfluidization

The emulsification is prepared in two steps:

1) A preemulsification by Ultra Turrax with slow addition of the fluorocarbon (1 min, 8000 t/min) to the solution of surfactant; and stirring for 6 min at 24000 t/min.

2) Emulsification by Microfluidizer. Measurement of the particle sizes by the photosedimentation method is made at each 5th pass until the smallest size and the best distribution are obtained. An emulsion of the same formulation, prepared with Pluronic F-68 as surfactant, required a greater number of passes to obtain a comparable distribution (Table IX).

What is claimed is:

1. A fluorinated compound having the formula:

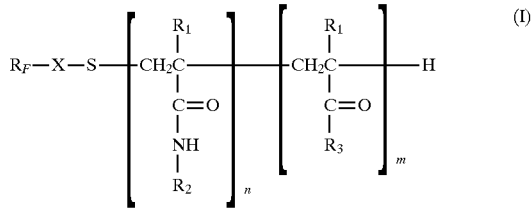

in which $R_F$ is a $C_2$–$C_{18}$ fluorinated radical;

X is an $C_1$–$C_{24}$ alkylene or fluoroalkylene group, linear or branched, having at least one subsitituent independently selected from the group consisting of —CON(R')—, —SO$_2$N(R')—, —S—, —O— or —N(R')— wherein R' is H or a $C_1$ to $C_6$ alkyl or fluoroalkyl radical; and when X is branched, a part of X can be $R_F$;

$R^1$ is H or CH$_3$;

$R^2$ is selected from the group consisting of the radicals (CH$_2$)$_p$—C(CH$_2$OH)$_3$, wherein p=0 to 3;

Z—$R_4$, wherein Z is a monovalent or bivalent radical selected from the group consisting of —NH—, —(CH$_2$)$_r$—N—(R$^1$)—, —(CH$_2$)$_r$—O—, or (CH$_2$)$_r$—S—, wherein r=2 to 4, and $R^1$ is as defined above; and $R^4$ is a monovalent radical derived from an ose, an oside or an amine derivative thereof;

$R^3$ is a amino acid residue obtained by removal of a hydrogen atom from the NH$_2$ group thereof;

n=1 to 50, provided that $R^2$ is (CH$_2$)$_p$—C(CH$_2$OH)$_3$ when n=1;

and m=0 or 1 to 200, provided that $0.2 \leq n/n+m \leq 1$.

2. A fluorinated compound according to claim 1, wherein $R_F$ is the radical F—(CF$_2$)$_t$—, wherein t=4 to 18.

3. A fluorinated compound according to claim 1 or 2, wherein X represents —CH$_2$— CH$_2$—.

4. A fluorinated compound according to claim 1 or 2, wherein X represents

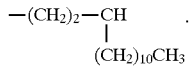

5. A fluorinated compound according to claim 1, wherein $R_1$ represents H.

6. A fluorinated compound according to claim 1, wherein $R_1$ represents CH$_3$.

7. A fluorinated compound according to claim 1, wherein $R_2$ represents —C(CH$_2$OH)$_3$.

8. A fluorinated compound according to claim 1, wherein $R_2$ represents the glucosyl, galactosyl, or glucaminyl radical.

9. A fluorinated compound according to claim 1 wherein $R_2$ is —Z—$R_4$, wherein Z is a monovalent or bivalent radical selected from the group consisting of —NH—, —(CH$_2$)$_r$—N—(R$_1$)—, —(CH$_2$)$_r$—O—, or (CH$_2$)$_r$—S—, wherein r=2 to 4, and $R_4$ is the lactobionyl, maltosyl or cellobiosyl radical.

10. A fluorinated compound according to claim 1 wherein n=1 to 20.

11. A method for synthesizing a telomeric compound according to claim 1, wherein m=0, comprising reacting a monomer having the formula

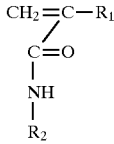

with a telogen of type $R_F$—X—SH, wherein $R_F$ is a $C_2$–$C_{18}$ fluorinated radical;

X is an $C_1$–$C_{24}$ alkylene or fluoroalkylene group, linear or branched, having at least one subsitituent independently selected from the group consisting of —CON(R')—, —SO$_2$N(R')—, —S—, —O— or —N(R)— wherein R' is H or a $C_1$ to $C_6$ alkyl or fluoroalkyl radical; and when X is branched, a part of X can be $R_F$;

$R_1$ is H or CH$_3$;

$R_2$ is selected from the group consisting of the radicals (CH$_2$)$_p$—C(CH$_2$OH)$_3$, wherein p=0 to 3;

Z—$R_4$, wherein Z is a monovalent or bivalent radical selected from the group consisting of —NH—, —(CH$_2$)$_r$—N—(R$_1$)—, —(CH$_2$)$_r$—O—, or (CH$_2$)$_r$—S—, wherein r=2 to 4, and $R_1$ is as defined above; and $R_4$ is a monovalent radical derived from an ose, an oside or an amine derivative thereof;

n=1 to 50, provided that $R_2$ is (CH$_2$)$_p$—C(CH$_2$OH)$_3$ when n=1; and m=0 under conditions serving to polymerize said monomer whereby said telomeric compound is formed.

12. A method for synthesizing a telomeric compound according to claim 1, wherein m>0, comprising reacting a monomer having the formula

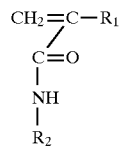

and a monomer having the formula

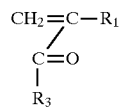

with a telogen of type $R_F$—X—SH, wherein

RF is a $C_2$–$C_{18}$ fluorinated radical;

X is an $C_1$–$C_{24}$ alkylene or fluoroalkylene group, linear or branched, having at least one substituent independently selected from the group consisting of —CON(R')—, —SO$_2$N(R')—, —S—, —O— or —N(R')— wherein R' is H or a $C_1$ to $C_6$ alkyl or fluoroalkyl radical; and when X is branched, a part of X can be $R_F$;

$R_1$ is H or CH$_3$;

$R_2$ is selected from the group consisting of the radicals (CH$_2$)$_p$—C(CH$_2$OH)$_3$, wherein p=0 to 3;

Z—$R_4$, wherein Z is a monovalent or bivalent radical selected from the group consisting of —NH—, —(CH$_2$)$_r$—N—(R$_1$)—, —(CH$_2$)$_r$—O—, or (CH$_2$)$_r$—S—, wherein r=2 to 4, and $R_1$ is as defined above; and $R_4$ is a monovalent radical derived from an ose, an oside or an amine derivative thereof;

$R_3$ is an amino acid residue obtained by removal of a hydrogen atom from the NH$_2$ group thereof;

n=1 to 50, provided that $R_2$ is (CH$_2$)$_p$—C(CH$_2$OH)$_3$ when n=1; and m=1 to 200, provided that $0.2 \leq n/n+m \leq 1$ under conditions serving to polymerize said monomers whereby said telomeric compound is formed.

* * * * *